(12) United States Patent
Matsumoto

(10) Patent No.: US 9,113,821 B2
(45) Date of Patent: Aug. 25, 2015

(54) RADIATION IMAGING APPARATUS AND METHOD

(71) Applicant: CANON KABUSHIKI KAISHA, Tokyo (JP)

(72) Inventor: Kazuhiro Matsumoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 22 days.

(21) Appl. No.: 13/948,993

(22) Filed: Jul. 23, 2013

(65) Prior Publication Data

US 2014/0029722 A1    Jan. 30, 2014

(30) Foreign Application Priority Data

Jul. 25, 2012 (JP) ................................. 2012-164740

(51) Int. Cl.
| | |
|---|---|
| *H05G 1/54* | (2006.01) |
| *A61B 6/10* | (2006.01) |
| *A61B 6/00* | (2006.01) |
| *A61B 6/06* | (2006.01) |

(52) U.S. Cl.
CPC ............. *A61B 6/107* (2013.01); *A61B 6/4441* (2013.01); *A61B 6/461* (2013.01); *A61B 6/54* (2013.01); *A61B 6/06* (2013.01); *A61B 6/469* (2013.01); *A61B 6/547* (2013.01)

(58) Field of Classification Search
CPC ....... G01N 23/00; G01N 23/04; G01N 23/06; G01N 23/083; H05G 1/58; H05G 1/60; A61B 6/10; A61B 6/54; A61N 5/1049
USPC ................................... 378/62, 98.2, 117, 205
See application file for complete search history.

(56) References Cited

FOREIGN PATENT DOCUMENTS

| | | |
|---|---|---|
| JP | 2005027806 A | 2/2005 |
| JP | 2010194057 A | 9/2010 |

*Primary Examiner* — Jurie Yun
(74) *Attorney, Agent, or Firm* — Canon USA Inc. IP Division

(57) ABSTRACT

A radiation imaging apparatus includes a radiation generation unit configured to radiate radiation to an object, a radiation detection unit configured to detect the radiation having passed through the object, an irradiation size detection unit configured to detect a size of an irradiation range of the radiation radiated by the radiation generation unit, a movement detection unit configured to detect a relative movement of the radiation generation unit and the radiation detection unit with respect to the object, and a control unit configured to control irradiation of the radiation to the object performed by the radiation generation unit. The control unit resumes, after a stop of the irradiation of the radiation, the irradiation of the radiation to the object performed by the radiation generation unit according to the relative movement detected by the movement detection unit and the size of the irradiation range detected by the irradiation size detection unit.

17 Claims, 8 Drawing Sheets

FINAL RADIATION IMAGE

RADIATION IMAGING APPARATUS AND METHOD

BACKGROUND OF THE INVENTION

1. Field of the Invention

The present invention relates to a radiation imaging apparatus, a control method, and a storage medium storing a computer program.

2. Description of the Related Art

There is known a radiation imaging apparatus that captures a radiation image based on detection of radiation (e.g., X-rays) having passed through an object. For example, the radiation imaging apparatus captures an image of an imaging target region, such as a digestive tract, by radiation. The radiation imaging apparatus is widely used not only for inspection during medical treatment but also for routine medical checkup.

There are various types of radiation imaging apparatuses. For example, Japanese Patent Application Laid-Open Nos. 2005-027806 and 2010-194057 discuss apparatuses that, while positioning an object placed on a top board of a bed between an X-ray generation apparatus and an X-ray detection apparatus attached to both ends of a support member referred to as a C arm, radioscopically view and capture an image of the object. X-rays emitted from the X-ray generation apparatus pass through the object to enter the X-ray detection apparatus. The X-ray detection apparatus converts the X-rays having passed through the object into an electric signal. By performing such an operation under a predetermined X-ray irradiation condition, the captured image or the radioscopically viewed object can be displayed on a monitor in real time.

In the case of the X-ray imaging apparatus, operations concerning radioscopical viewing and imaging performed by an operator are roughly classified into the steps of: (1) positioning carried out while performing radioscopical viewing; (2) diagnosis in a radioscopically viewed state (checking of an imaging target region); and (3) imaging of a positioned region.

In the step (1) "positioning carried out while performing radioscopical viewing", the positioning is performed so that the imaging target region can be displayed with a desired size at an appropriate position (e.g., a center position) of the monitor. During the positioning, the operator moves at least one of the X-ray generation apparatus, the X-ray detection apparatus, and the top board.

In other words, since the operator moves such a unit during the positioning, the image (observed image) displayed on the monitor moves. On the other hand, in the step (2) "diagnosis in a radioscopically viewed state (checking of an imaging target region)", the operator does not perform any positioning operation. The position of the observed image on the monitor is in a fixed state.

Then, when the operator visually confirms the imaging target region, the step (3) "imaging of a positioned region" is performed under the predetermined X-ray irradiation condition. During X-ray imaging, the operation steps of (1) to (3) are repeated.

Generally, in a medical modality that uses X-rays, how to shorten a time for radioscopical viewing and imaging or how to reduce an X-ray exposure dose of the object is an important control item and a research item.

For example, in the "positioning carried out while performing radioscopical viewing", if an image displayed on the monitor moves on the monitor interlockingly with only the operator's positioning operation, the positioning operation can be continued without any radioscopical viewing, and the X-ray exposure dose of the object can be reduced.

SUMMARY OF THE INVENTION

The present invention is directed to an improvement of operability during a positioning operation, and a reduction of an X-ray exposure dose of an object by performing radiation irradiation and imaging necessary for a positioning operation of an imaging target region at necessary and sufficient timing.

According to an aspect of the present invention, a radiation imaging apparatus includes a radiation generation unit configured to radiate radiation to an object, a radiation detection unit configured to detect the radiation having passed through the object, an irradiation size detection unit configured to detect a size of an irradiation range of the radiation radiated by the radiation generation unit, a movement detection unit configured to detect a relative movement of the radiation generation unit and the radiation detection unit with respect to the object, and a control unit configured to control irradiation of the radiation to the object performed by the radiation generation unit, wherein the control unit resumes, after a stop of the irradiation of the radiation, the irradiation of the radiation to the object performed by the radiation generation unit according to the relative movement detected by the movement detection unit and the size of the irradiation range detected by the irradiation size detection unit.

Further features of the present invention will become apparent from the following detailed description of exemplary embodiments with reference to the attached drawings.

DESCRIPTION OF THE EMBODIMENTS

Various exemplary embodiments, features, and aspects of the invention will be described in detail below with reference to the drawings.

The exemplary embodiments will be described by taking an example where an X-ray is applied as radiation. Not limited to the X-ray, however, an electromagnetic wave, an α-ray, a β-ray, or a γ-ray can be used. The exemplary embodiments will be described by taking an example of an X-ray imaging apparatus on which a C arm is mounted as a radiation imaging apparatus. In this X-ray imaging apparatus, imaging is performed while moving or rotating an imaging system configured by connecting an X-ray generation unit and an X-ray detection unit to each other. Not limited to the X-ray imaging apparatus of this type, the present invention can be applied to, for example, a table-type X-ray imaging apparatus referred to as a radio frequency (RF) imaging apparatus.

Figure 1:
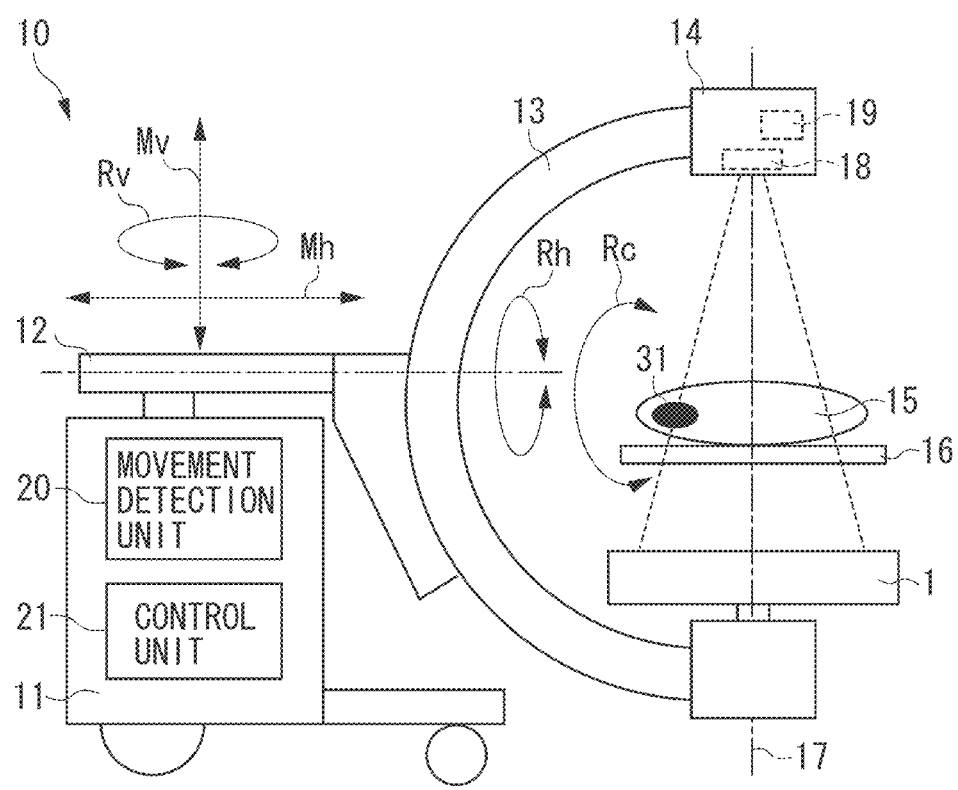
FIG. 1 illustrates an example of a configuration of an X-ray imaging apparatus.

FIG. 1 illustrates an example of a configuration of an X-ray imaging apparatus 10 according to a first exemplary embodiment.

The X-ray imaging apparatus 10 includes a single or a plurality of computers. The computer functions as a control unit 21 described below, and includes a central processing unit (CPU), a read only memory (ROM), and a random access memory (RAM). The X-ray imaging apparatus 10 can include a communication unit such as a network card, an input unit such as a keyboard or a mouse, a display unit such as a monitor, and an input/output unit such as a touch panel. These components are interconnected via a bus, and controlled by executing a program stored in the ROM by the CPU.

The X-ray imaging apparatus 10 includes a body unit 11, a horizontal shaft 12, and a C arm 13. The horizontal shaft 12 is supported on the body unit 11, and moves and rotates with respect to the body unit 11. The C arm 13 is disposed at a leading end of the horizontal shaft 12, and includes a C-shaped arm member. The horizontal shaft 12 and the C arm 13 rotate in illustrated arrow directions (arrows Rc, Rh, and Rv), and moves (arrows Mh and Mv).

An X-ray generation unit 14 and an X-ray detection unit 1 are arranged to face each other at both ends of the C arm 13. The C arm 13 supports the X-ray generation unit 14 and the X-ray detection unit 1 to keep a fixed distance therebetween. The X-ray generation unit 14 and the X-ray detection unit 1 are arranged at arbitrary positions and angles to an object 15 by a movable mechanism (not illustrated).

The X-ray generation unit 14, which functions as a radiation generation unit, radiates radiation (X-rays) to the object (e.g., a human body) 15 (exposure). The X-ray detection unit 1, which functions as a radiation detection unit, detects the X-rays having passed through the object. The object 15 is supported on a top board 16, which functions as an object supporting unit. The top board 16 is located between the X-ray generation unit 14 and the X-ray detection unit 1. A virtual axis 17 is an X-ray irradiation axis connecting the center of an effective imaging range of X-rays detection unit 1 to the X-ray generation unit 14.

The X-ray generation unit 14 includes a diaphragm 18. The diaphragm 18 functions as a diaphragm mechanism for adjusting an X-ray dose (radiation dose). An irradiation range (especially, the size of an irradiation region) of X-rays is changed by this mechanism. The diaphragm 18 includes a shield (e.g., made of heavy metal having a high X-ray shielding ratio) to adjust the X-ray dose. Accordingly, the X-ray generation unit 14 radiates X-rays to the object 15 in an optimal shape according to an imaging target region. The diaphragm 18 can be configured by, for example, arranging two sets of shielding mechanisms for changing an opening width by two shields orthogonal to each other (rectangular configuration). A circular or polygonal shape can also be employed. Further, the X-ray generation unit 14 includes an irradiation size detection unit 19 for detecting the size of an irradiation range. The irradiation size detection unit 19 detects the size of an irradiation range based on the opening width of the diaphragm 18 and the distance between the X-ray generation unit 14 and the X-ray detection unit 1.

The body unit 11 includes, as functional components, for example, a movement detection unit 20 and a control unit 21. The movement detection unit 20 detects information (e.g., moving direction, moving amount, and moving speed) about movement or rotation of the horizontal shaft 12. Specifically, the movement detection unit 20 detects movement of the horizontal shaft 12 in the Mh direction and the My direction or rotation of the horizontal shaft 12 in the Rv direction. For the movement detection unit 20, for example, a linear encoder can be used. The control unit 21 performs control of the X-ray imaging apparatus 10 including operation (diaphragm) control of the diaphragm 18 and display control of a captured radiation image on a monitor (not illustrated), and storage of the captured radiation image.

In the X-ray imaging apparatus 10, an operator performs a positioning operation so that an image of a desired imaging target region 31 of the object 15 can be captured while the operator observes the radiation image displayed on the monitor.

Figure 2A:
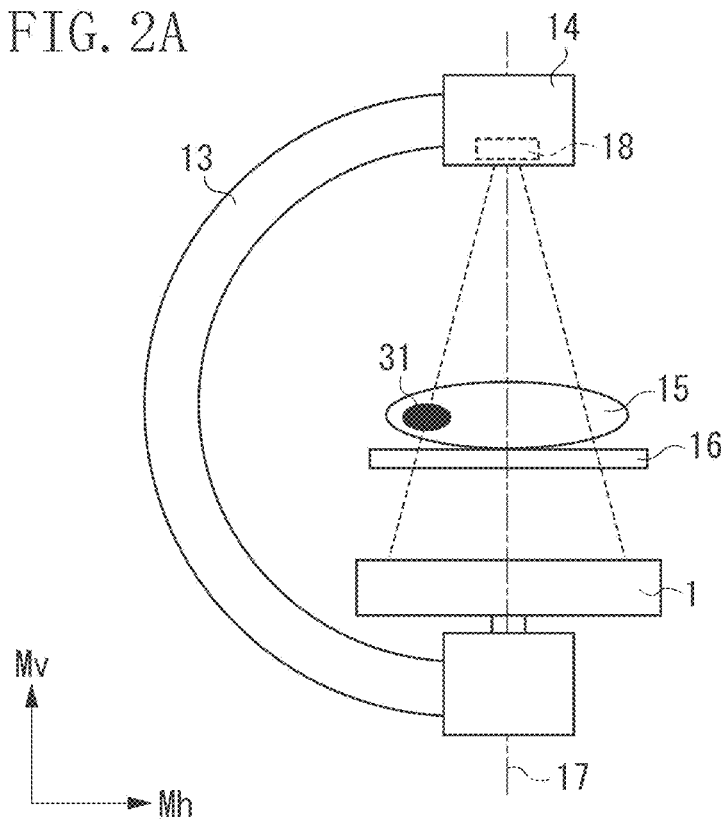
FIGS. 2A and 2B illustrate examples of a positional relationship between a C arm and a desired imaging target region and a display state of a monitor.
Figure 2B:
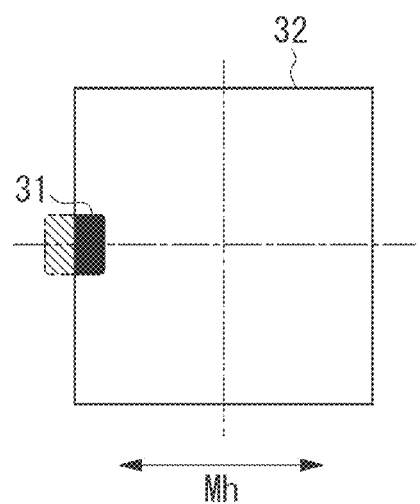
Figure 3A:
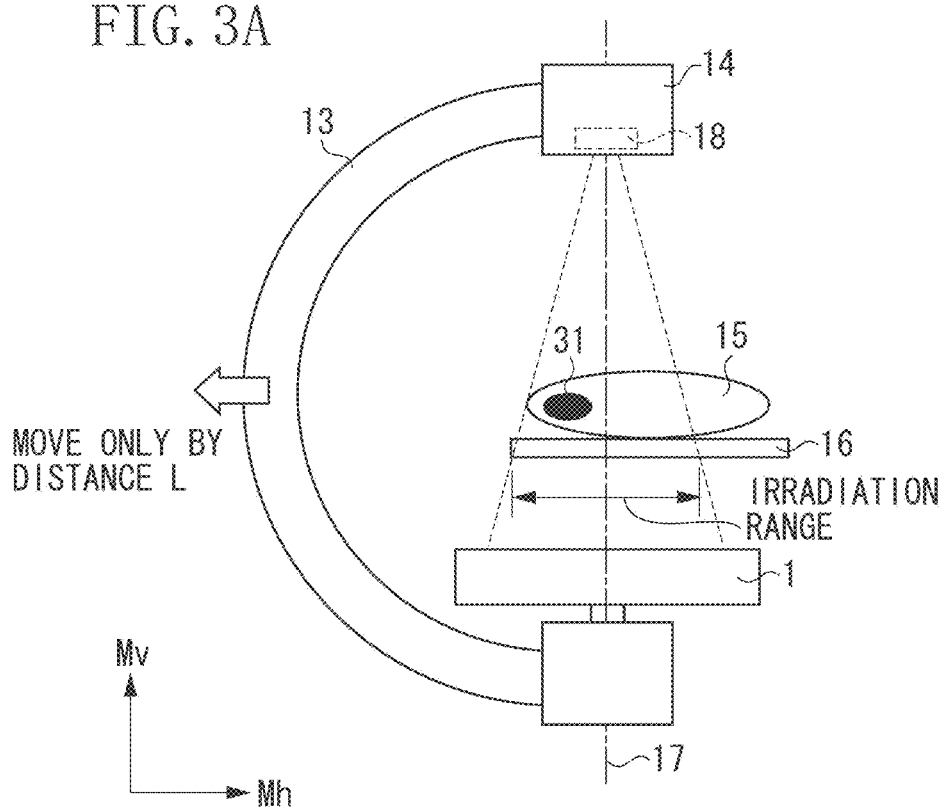
FIGS. 3A and 3B illustrate examples of a positional relationship between the C arm and a desired imaging target region and a display state of the monitor.
Figure 3B:
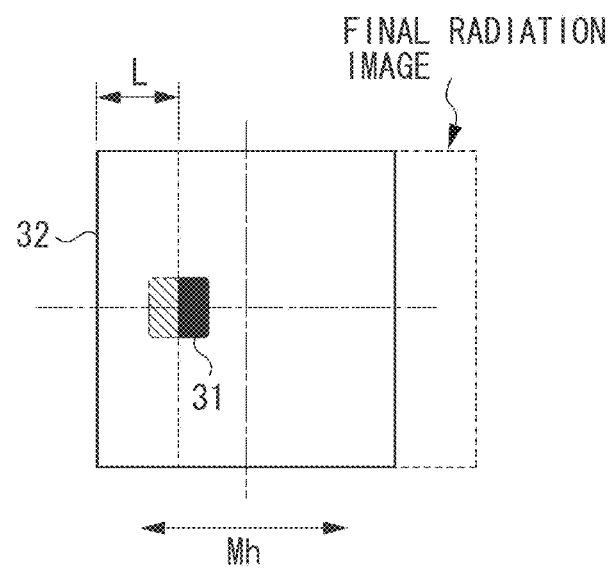
Figure 4A:
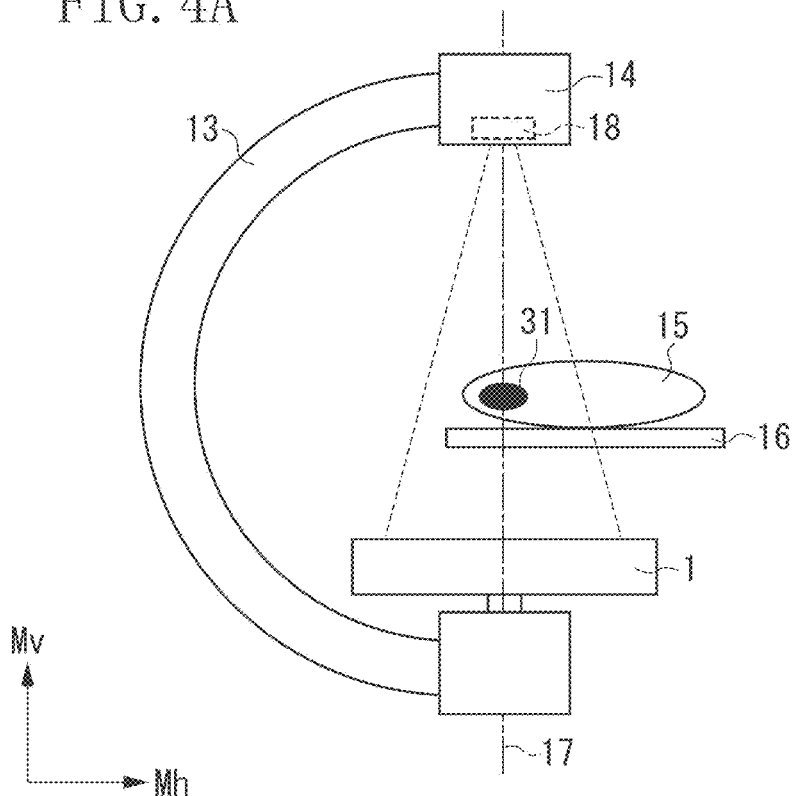
FIGS. 4A and 4B illustrate examples of a positional relationship between the C arm and a desired imaging target region and a display state of the monitor.
Figure 4B:
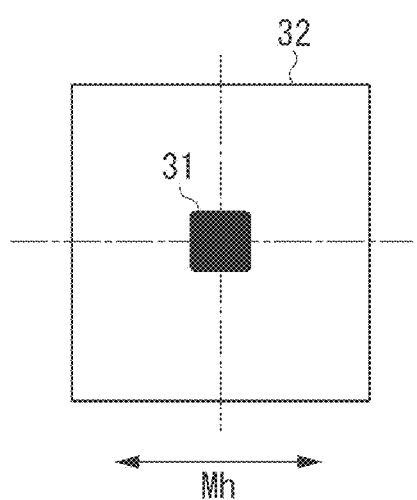

Next, referring to FIGS. 2A and 2B to FIGS. 4A and 4B, imaging control processing during the positioning operation of the present exemplary embodiment will be described. Each of FIGS. 2A, 3A, and 4A illustrates a positional relationship between the C arm and a desired imaging target position. FIGS. 2B, 3B, and 4B illustrate monitor displays corresponding to FIGS. 2A, 3A, and 4A.

It is supposed that the object 15 is radioscopically viewed in the positional relationship between its desired imaging target region 31 and the X-ray imaging apparatus 10 illustrated in FIG. 2A. In this case, since the X-rays are radiated only to a right side portion of the desired imaging target region 31, as illustrated in FIG. 2B, only the right side portion (black portion) of the desired imaging target region 31 in an entire image 32 is displayed on the monitor. A left side portion (hatched portion) of the desired imaging target region 31 is not displayed on the monitor because it is not irradiated with any X-ray. When the desired imaging target region 31 is moved near the center of the irradiation range of X-rays to observe the entire desired imaging target region 31, the operator moves the C arm 13 in the Mh direction (more specifically, a direction away from the object 15). Accordingly, the control unit 21 moves the X-ray generation unit 14 and the X-ray detection unit 1 relative to the object 15. The control unit 21 stops the X-ray irradiation after the movement of the C arm 13 has been started, stores a final radiation image captured immediately before the stop of the X-ray irradiation in, for example, the RAM of the control unit 21, and simultaneously displays the image on the monitor. When the C arm 13 is continuously moved according to an operator's operation, the control unit 21 continuously displays the final radiation image on the monitor while shifting the final radiation image on the monitor. The control unit 21 determines a shifting direction and a shifting amount of the final radiation image on the monitor interlockingly with a detection result of the movement detection unit 20. In other words, in the present exemplary embodiment, the control unit 21 moves the final radiation image (dotted-line portion) in the right direction illustrated in FIG. 3B to display the final radiation image on the monitor according to, during the movement of the C arm 13, a moving direction and a moving amount of the C arm 13 illustrated in FIG. 3A.

To continue positioning, the X-ray irradiation needs to be resumed before the C arm 13 moves over the irradiation range of X-rays and the final radiation image is not displayed at all on the monitor. Specifically, in the present exemplary embodiment, the control unit 21 resumes the X-ray irradiation to display the radiation image on the monitor when the moving direction and the moving amount of the C arm 13 are set in a predetermined relationship with the X-ray irradiation range of the final radiation image. In the example illustrated in FIG. 4A, the control unit 21 performs control to resume the irradiation when the C arm 3 is moved by a distance about half of the X-ray irradiation range of the final radiation image as illustrated in FIG. 4A. Thus, the control unit 21 radiates X-rays to the entire desired imaging target region in a state illustrated in FIG. 4A, and displays the radiation image on the monitor as illustrated in FIG. 4B.

Figure 5:
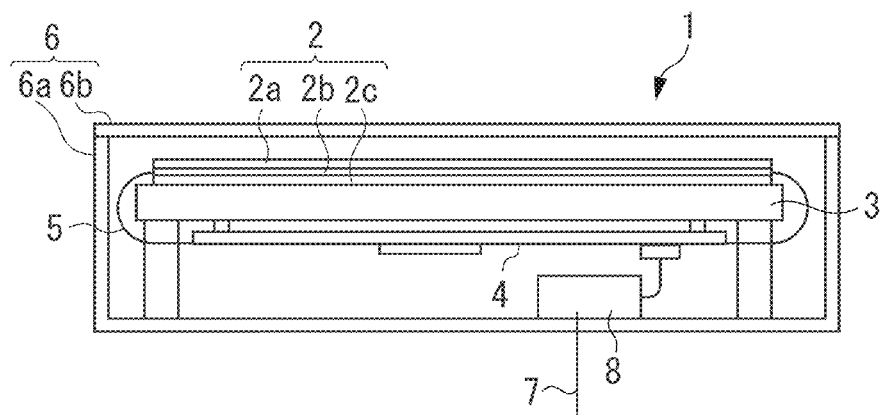
FIG. 5 illustrates an example of a sectional configuration of the inside of an X-ray detection unit.

Next, referring to FIG. 5, an example of a sectional configuration of the inside of the X-ray detection unit 1 illustrated in FIG. 1 will be described. A detection panel 2 is used to detect X-rays having passed through the object. The detection panel 2 includes a fluorescent screen 2a, a photoelectric conversion element 2b, and a substrate 2c. For the substrate 2c, for example, a glass plate can be used. The photoelectric conversion element 2b is two-dimensionally (one-dimensionally) arrayed on the substrate 2c. A read circuit for reading a photoelectrically converted electric signal or a drive circuit for selecting an element that is a reading target is connected to an end of the detection panel 2. The detection panel 2 is, for example, rectangular, and the read circuit and the drive circuit are arranged at sides orthogonal to each other.

For the fluorescent screen 2a, for example, a screen prepared by applying a fluorescent substance made of a metal compound on a resin plate is used. The fluorescent screen 2a is formed integrally with the substrate 2c, and fixed as the detection panel 2 to a metallic base 3. An electric board 4 is disposed on a rear side of the base 3. The electric board 4 generates an X-ray image (radiation image) based on an electric signal acquired from the detection panel 2. The electric board 4 is connected to the detection panel 2 via a flexible circuit board 5.

The base 3 is fixed to a casing 6a. The X-ray detection unit 1 is sealed with a casing lid 6b made of a material having high X-ray permeability. The X-ray detection unit 1 is connected to the control unit 21 via a cable 7 and a relay electric circuit unit 8. Accordingly, the X-ray detection unit 1 supplies power or transfers a signal.

As described above, the X-ray detection unit 1 captures a radiation image based on X-rays having passed through the object. When the X-rays having passed through the object enter the X-ray detection unit 1, the fluorescent substance of the fluorescent screen 2a emits light, and the two-dimensionally arrayed photoelectric conversion element 2b converts the light into an electric signal. Then, the electric signal is transferred as electric image information to the control unit 21 via the cable 7. The control unit 21 displays the image information on the monitor, thus enabling the operator to observe the radiation image in real time.

Figure 6:
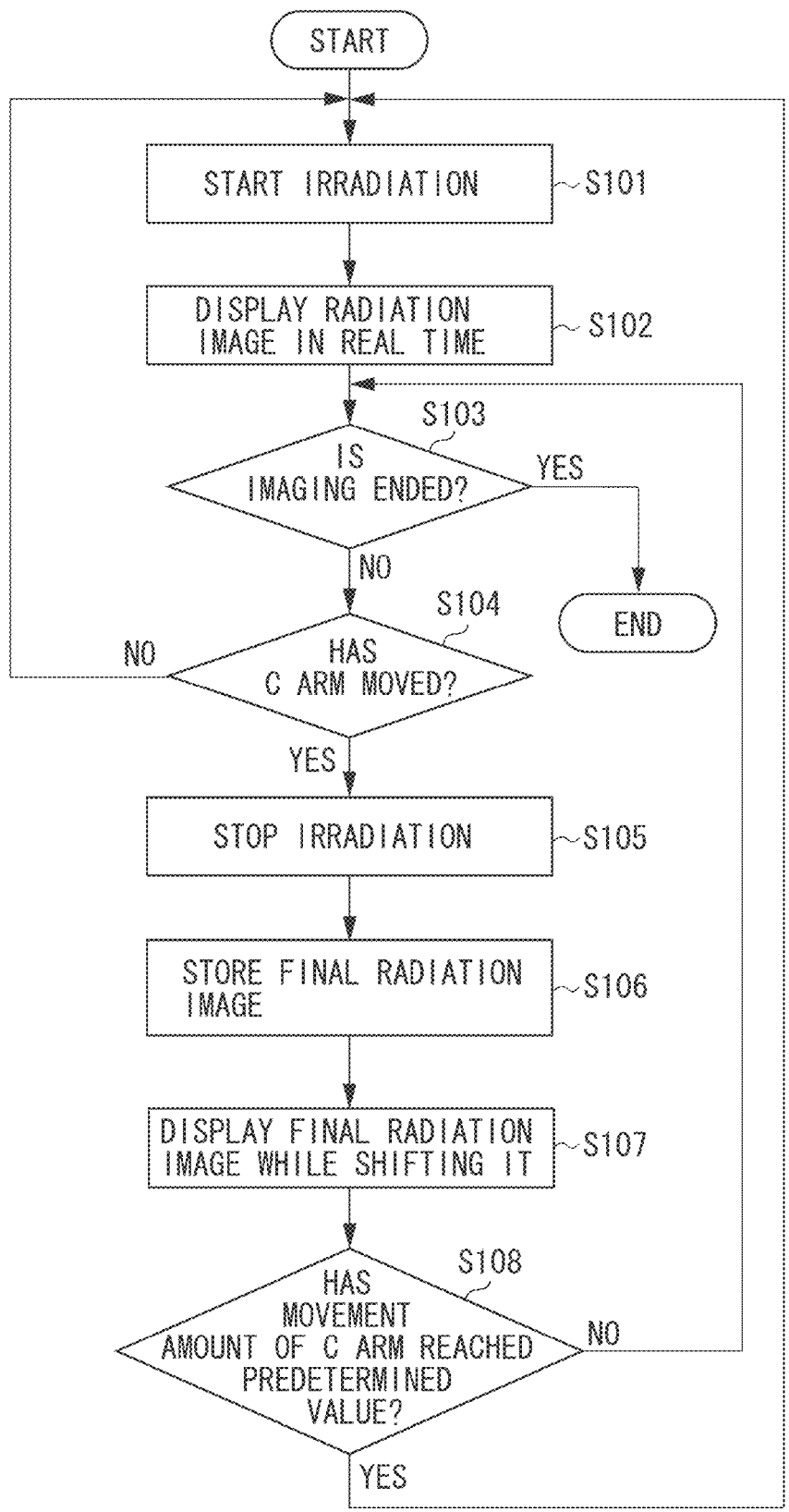
FIG. 6 is a flowchart illustrating an example of an imaging operation according to a first exemplary embodiment.

Next, referring to the flowchart of FIG. 6, an example of an imaging operation at the X-ray imaging apparatus 10 will be described.

After a start of radioscopical viewing has been instructed by the operator (or automatically), in step S101, the control unit 21 of the X-ray imaging apparatus 10 starts radioscopical viewing of the object 15. Specifically, the X-ray generation unit 14 radiates X-rays to an X-ray object (e.g., a human body), and the X-ray detection unit 1 continuously captures radiation images based on the X-rays having passed through the object. In step S102, as illustrated in FIG. 2B, the control unit 21 displays a radiation image within a predetermined irradiation range on the monitor in real time. Then, in step S103, the control unit 21 determines whether an end of the imaging has been instructed by the operator (or automatically). When instructed (YES in step S103), the control unit 21 ends the imaging processing. When not instructed (NO in step S103), the control unit 21 continuously monitors movement of the C arm 13 during the imaging. Specifically, in step S104, the control unit 21 detects information about movement or rotation of the horizontal shaft 12 from the movement detection unit 20, and determines whether the C arm 13 has moved. When there is no change in detection result of the movement detection unit 20, the control unit 21 determines that the C arm 13 has not moved (NO in step S104), and maintains the current X-ray irradiation and the real-time displaying state of the radiation image (steps S101 and S102). On the other hand, when there is a change in detection result of the movement detection unit 20, the control unit 21 determines that the C arm 13 has moved (YES in step S104). Then, in step S105, the control unit 21 stops the X-ray irradiation. In step S106, the control unit 21 stores a final radiation image in its RAM. This processing corresponds to an example of processing performed by a storage unit. The final radiation image is an image captured when the X-ray irradiation is stopped (immediately before stop).

Then, in step S107, the control unit 21 displays the final radiation image on the monitor while continuously shifting the final radiation image according to the movement of the C arm 13 (a detection result of the movement detection unit 20). For example, when the C arm 1 is moved in a direction (left) away from the object 15 in the Mh direction as illustrated in FIG. 3A, as illustrated in FIG. 3B, the control unit 21 displays the final radiation image on the monitor while shifting the final radiation image in the right direction. As illustrated in FIG. 3B, in the case of a moving distance L of the C arm 13, the final radiation image displayed on the monitor changes by an amount equivalent to the distance L. The distance L is about ¼ of the size of the irradiation range of X-rays in the Mh direction.

Thus, the control unit 21 displays a relative positional relationship between the desired imaging target region 31 and the irradiation range of X-rays without radiating any X-ray to the desired imaging target region 31. The control unit 21 continuously displays the final radiation image according to the movement of the C arm 13. For example, when the moving direction of the C arm 13 changes to a direction opposite that thus far, the control unit 21 moves the final radiation image moved right in the left direction.

In step S108, the control unit 21 determines whether a moving amount of the C arm 13 has reached a predetermined value. When it is detected that the moving amount of the C arm 13 has reached the predetermined value (YES in step S108), the control unit 21 returns to step S101, in which the control unit 21 resumes the X-ray irradiation as illustrated in FIGS. 4A and 4B. Then, even when the C arm 13 stops (YES in step S104), the processing returns to step S101, and the control unit 21 continues the X-ray irradiation.

On the other hand, when it is detected that the moving amount of the C arm 13 has not reached the predetermined value (NO in step S108), the control unit 21 returns to step S103. Then, the control unit 21 repeats the processing until the end of imaging.

In the present exemplary embodiment, control is performed to resume the irradiation when the moving amount of the C arm 13 is ½ of the size of the irradiation range of X-rays during capturing of the final radiation image, in other words, the desired imaging target region 31 is located at the center of the irradiation range of X-rays. Accordingly, in FIGS. 4A and 4B, the desired imaging target region 31 displayed on the center of the monitor is a radiation image captured by resuming the X-ray irradiation. The size of the irradiation range of X-rays during capturing of the final radiation image is based on a detection result of the irradiation size detection unit 19.

The moving amount of the C arm 13 where the X-ray irradiation is resumed in the present exemplary embodiment is an example. The moving amount can be arbitrarily set based on the size of the irradiation range of X-rays according to an imaging purpose. For example, the X-ray imaging apparatus 10 can be configured such that the operator inputs (including selection) resumption of irradiation based on a moving amount, namely, "⅓" of the size of the irradiation range to the control unit 21 via the input unit. In this case, "⅓" is referred to as an irradiation resumption size ratio. The control unit 21 obtains the size of the irradiation range of the final radiation image from the irradiation size detection unit 19, and calculates a distance obtained by multiplying a distance of, for example, one side of the obtained size of the irradiation range with the input irradiation resumption size ratio ("⅓"). The control unit 21 can set the calculated distance as a predetermined value for determining whether to resume the irradiation.

Not limited to the case where the operator inputs the irradiation resumption size ratio, the X-ray imaging apparatus 10 can be configured such that sizes of exposure doses can be input at stages or continuously (including selection). In this case, a table storing an exposure dose "small" associated with resumption of irradiation at a moving amount of, for example, "½" of the size of the irradiation range and an exposure dose "large" associated with resumption of irradiation at a moving amount of, for example, "¼" of the size of the irradiation range is stored beforehand in the ROM. The control unit 21 obtains, from the input size of the exposure dose, an irradiation resumption size ratio ("½" or "¼") to resume irradiation by referring to the table. The control unit 21 can set a predetermined value for determining whether to resume the irradiation by performing processing similar to that described above by using the obtained irradiation resumption size ratio.

Further, for example, the X-ray imaging apparatus can be configured such that the operator inputs an "imaging purpose (including an imaging target region)" to the control unit 21 via the input unit (including selection). In this case, a table storing an "imaging purpose" associated with an irradiation resumption size ratio ("½" or "¼") where irradiation is resumed is stored beforehand in the ROM. The control unit 21 obtains, from the input "imaging purpose", an irradiation resumption size ratio ("½" or "¼") to resume irradiation by referring to the table. The control unit 21 can set a predetermined value for determining whether to resume the irradiation by performing processing similar to that described above by using the obtained irradiation resumption size ratio.

Thus, according to the present exemplary embodiment, a period of radiating X-rays is automatically determined according to the operator's positioning operation. More specifically, the control unit 21 controls presence of irradiation of X-rays based on the size of the irradiation range of X-rays and the relative position information (moving amounts) of the X-ray generation unit 14 and the X-ray detection unit 1 to the object. As a result, since irradiation timing is automatically controlled, operability during the positioning operation can be improved, and the X-ray exposure dose of the object can be reduced.

In the present exemplary embodiment, the control unit 21 determines whether to resume irradiation of radiation from the irradiation stopped state of radiation according to the size of the irradiation range detected by the irradiation size detection unit 19 in addition to the relative moving amount of the X-ray generation unit 14 and the X-ray detection unit 15 with respect to the object. In other words, the control unit 21 can perform control, for example, even if the relative moving amount is equal, not to resume the irradiation of radiation when the size of the irradiation range is large and to resume the irradiation of radiation when the size of the irradiation range is small. By this control, the exposure dose of the object can be reduced according to the size of the irradiation range, and the irradiation of the radiation is resumed according to the size of the irradiation range. Thus, the operator can observe a desired radiation image.

Figure 7:
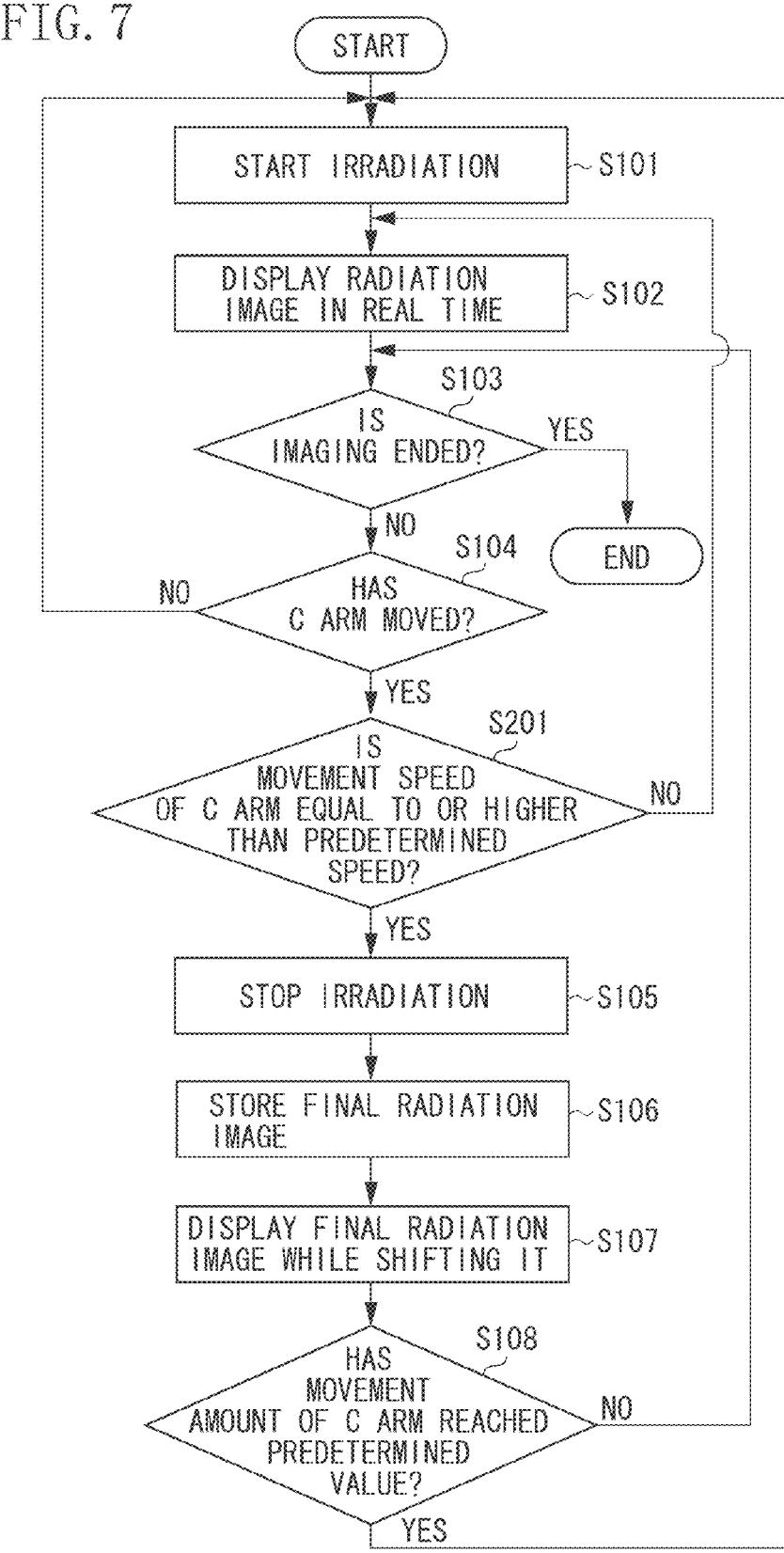
FIG. 7 is a flowchart illustrating an example of an imaging operation according to a second exemplary embodiment.

Next, referring to the flowchart of FIG. 7, an example of an imaging operation by the X-ray imaging apparatus 10 according to a second exemplary embodiment will be described. In the present exemplary embodiment, members and steps of the flowchart similar to those of the first exemplary embodiment will be denoted by similar reference numerals, and detailed description thereof will be omitted. In the flowchart of FIG. 7, steps S101 to S104 and steps S105 to S108 are similar to those of the flowchart of the first exemplary embodiment. In the present exemplary embodiment, step S201 is added between steps S104 and S105.

In step S201, the control unit 21 determines whether a moving speed of the C arm 13 is equal to or higher than a predetermined speed. This determination is performed based on a detection result of the movement detection unit 20. When the moving speed of the C arm 13 is equal to or higher than the predetermined speed (YES in step S201), in step S105, the control unit 21 stops X-ray irradiation. On the other hand, when the moving speed of the C arm 13 is lower than the predetermined speed (NO in step S201), the control unit 21 returns to step S102 to maintain a current irradiation state. Then, the control unit 21 repeats the processing until an end of the imaging. The present exemplary embodiment is based on an idea that when the moving speed is high, it is determined that a positioning operation is being performed at a rough position, and a necessity of displaying a radiation image in real time is not high. The predetermined speed for determining whether to stop the X-ray irradiation can be arbitrarily set based on the size of an irradiation range of X-rays.

For example, when the size of the irradiation range is large or an operator's level of operation skill is high, the control unit 21 can set the predetermined speed high. This processing corresponds to an example of processing of a setting unit. When the size of the irradiation range is large or an operator's level of operation skill is high, the predetermined speed set high will give no trouble to the positioning operation.

Thus, according to the present exemplary embodiment, as in the case of the first exemplary embodiment, since irradiation timing is automatically controlled, operability during the positioning operation can be improved, and an X-ray exposure dose of the object can be reduced. In the present exemplary embodiment, when the X-ray generation unit 14 and the X-ray detection unit 1 move relative to the object, the X-ray irradiation is stopped determining a rough positioning operation stage when the moving speed is equal to or higher than the predetermined speed. Thus, the X-ray exposure dose of the object can be reduced. When the moving speed is lower than the predetermined speed, the X-ray irradiation is continued determining a stage where the operator wishes to observe a radiation image. Thus, operability can be improved.

The exemplary embodiments of the present invention have been described. However, the present invention is not limited to the exemplary embodiments. Various changes and modifications can be made within the gist of the invention.

Figure 8A:
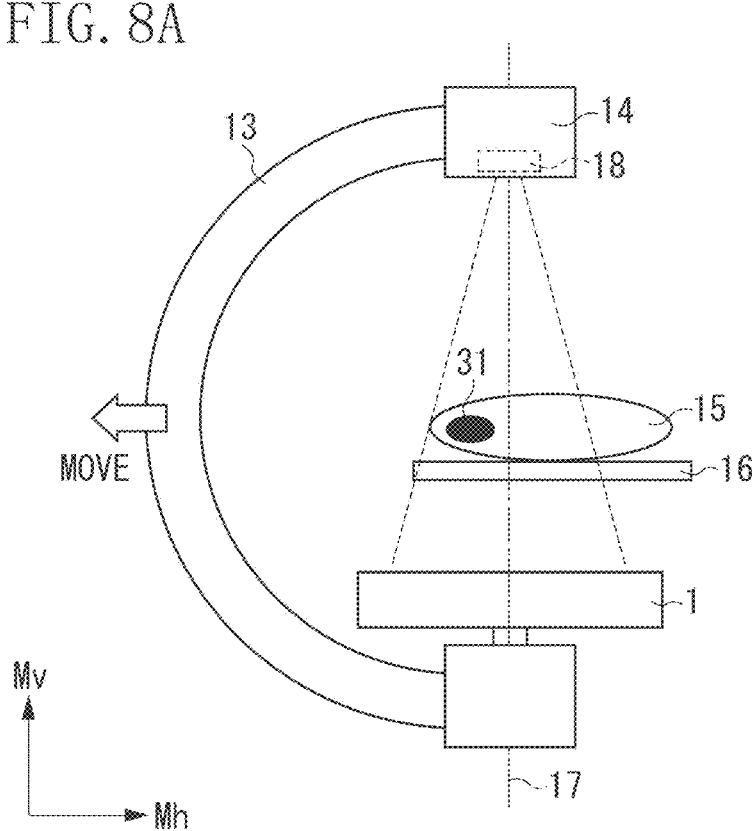
FIGS. 8A and 8B illustrate examples of a positional relationship between a C arm and a desired imaging target region and a display state of a monitor.
Figure 8B:
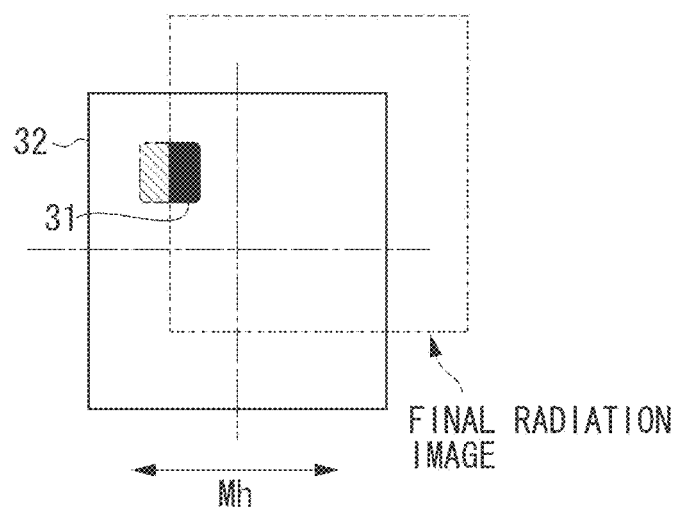

For example, the exemplary embodiment has been described by way of case where the period of performing X-ray irradiation is automatically determined according to the movement of the C arm 13 in the Mh direction, and the final radiation image displayed on the monitor is shifted to be displayed during the period where no X-ray irradiation is performed. However, the present invention can be applied when other positioning operations are performed. For example, even when the C arm 13 is rotated in the Rv direction or simultaneously moved or rotated in a plurality of directions, the period of performing X-ray irradiation can be automatically set. Specifically, as illustrated in FIG. 8A, it is when the C arm 13 is moved in a direction away from the object 15 in the Mh direction and toward the front side of the drawing plane. In this case, as illustrated in FIG. 8B, the final radiation image is displayed on the monitor while being shifted right.

The exemplary embodiment has been described by taking the example of the X-ray imaging apparatus 10 of the type where the top board 16 for supporting the object 15 is fixed and only the imaging system moves. However, the X-ray imaging apparatus is not limited to this type. The X-ray imaging apparatus can include a detection unit for detecting relative positions of the imaging system and the top board, changes of angles, and a moving speed. For example, the X-ray imaging apparatus can be a type where only the top board moves or a type where the imaging system and the top board both move. The imaging system and the top board can be moved manually or by electric power.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-164740 filed Jul. 25, 2012, which is hereby incorporated by reference herein in its entirety.

What is claimed is:

1. A radiation imaging apparatus comprising:
a radiation generation unit configured to radiate radiation to an object;
a radiation detection unit configured to detect the radiation having passed through the object;
an irradiation size detection unit configured to detect a size of an irradiation range of the radiation radiated by the radiation generation unit;
a movement detection unit configured to detect a relative movement of the radiation generation unit and the radiation detection unit with respect to the object; and
a control unit configured to control irradiation of the radiation to the object performed by the radiation generation unit,
wherein the control unit resumes, after a stop of the irradiation of the radiation, the irradiation of the radiation to the object performed by the radiation generation unit according to the relative movement detected by the movement detection unit and the size of the irradiation range detected by the irradiation size detection unit.

2. The radiation imaging apparatus according to claim 1, wherein, if the relative movement detected by the movement detection unit reaches a predetermined value set based on the size of the irradiation range detected by the irradiation size detection unit, the control unit resumes the irradiation of the radiation to the object performed by the radiation generation unit.

3. The radiation imaging apparatus according to claim 2, further comprising a setting unit configured to set a distance calculated based on an irradiation resumption size ratio input by an operator or an imaging purpose input by the operator and the size of the irradiation range detected by the irradiation size detection unit as the predetermined value for resuming the irradiation of the radiation.

4. The radiation imaging apparatus according to claim 1, further comprising a display control unit configured to display a radiation image of the radiation detected by the radiation detection unit on a display unit,
wherein the display control unit displays, on the display unit, the radiation image of the radiation detected by the radiation detection unit when the irradiation of the radiation to the object is stopped, and displays the radiation image while moving the radiation image according to the relative movement detected by the movement detection unit.

5. The radiation imaging apparatus according to claim 4, further comprising a storage unit configured to store the radiation image of the radiation detected by the radiation detection unit when the irradiation of the radiation to the object is stopped,
wherein the display control unit displays the radiation image stored by the storage unit while moving the radiation image according to the relative movement detected by the movement detection unit.

6. The radiation imaging apparatus according to claim 1, wherein, if the relative movement is detected by the movement detection unit and a speed of the relative movement is equal to or higher than a predetermined speed, the control unit stops the irradiation of the radiation to the object performed by the radiation generation unit.

7. The radiation imaging apparatus according to claim 6, further comprising a setting unit configured to set the predetermined speed based on the size of the irradiation range detected by the irradiation size detection unit.

8. A method for controlling a radiation imaging apparatus, the radiation imaging apparatus including:
a radiation generation unit configured to radiate radiation to an object;
a radiation detection unit configured to detect the radiation having passed through the object;
an irradiation size detection unit configured to detect a size of an irradiation range of the radiation radiated by the radiation generation unit;
a movement detection unit configured to detect a relative movement of the radiation generation unit and the radiation detection unit with respect to the object; and
a control unit configured to control irradiation of the radiation to the object performed by the radiation generation unit, the method comprising:
resuming, after a stop of the irradiation of the radiation, the irradiation of the radiation to the object performed by the radiation generation unit according to the relative movement detected by the movement detection unit and the size of the irradiation range detected by the irradiation size detection unit.

9. A non-transitory computer-readable storage medium storing a program that causes a computer to execute a method for controlling a radiation imaging apparatus,
the radiation imaging apparatus including:
a radiation generation unit configured to radiate radiation to an object;
a radiation detection unit configured to detect the radiation having passed through the object;
an irradiation size detection unit configured to detect a size of an irradiation range of the radiation radiated by the radiation generation unit;
a movement detection unit configured to detect a relative movement of the radiation generation unit and the radiation detection unit with respect to the object; and
a control unit configured to control irradiation of the radiation to the object performed by the radiation generation unit,
the method comprising:
resuming, after a stop of the irradiation of the radiation, the irradiation of the radiation to the object performed by the radiation generation unit according to the relative movement detected by the movement detection unit and the size of the irradiation range detected by the irradiation size detection unit.

10. A radiation imaging apparatus comprising:
a radiation generation unit configured to radiate radiation to an object;
a radiation detection unit configured to detect the radiation having passed through the object;
an irradiation detection unit configured to detect an irradiation range of the radiation radiated by the radiation generation unit;
a movement detection unit configured to detect a relative movement of the radiation generation unit and the radiation detection unit with respect to the object; and
a control unit configured to control irradiation of the radiation to the object performed by the radiation generation unit,
wherein the control unit resumes, after a stop of the irradiation of the radiation, the irradiation of the radiation to the object performed by the radiation generation unit according to the relative movement detected by the movement detection unit and the irradiation range detected by the irradiation detection unit.

11. The radiation imaging apparatus according to claim 10, wherein, if the relative movement detected by the movement detection unit reaches a predetermined value set based on the irradiation range detected by the irradiation detection unit, the control unit resumes the irradiation of the radiation to the object performed by the radiation generation unit.

12. The radiation imaging apparatus according to claim 11, further comprising a setting unit configured to set a distance calculated based on an irradiation resumption ratio input by an operator or an imaging purpose input by the operator and the irradiation range detected by the irradiation detection unit as the predetermined value for resuming the irradiation of the radiation.

13. The radiation imaging apparatus according to claim 10, further comprising a display control unit configured to display a radiation image of the radiation detected by the radiation detection unit on a display unit,
wherein the display control unit displays, on the display unit, the radiation image of the radiation detected by the radiation detection unit when the irradiation of the radiation to the object is stopped, and displays the radiation image while moving the radiation image according to the relative movement detected by the movement detection unit.

14. The radiation imaging apparatus according to claim 13, further comprising a storage unit configured to store the radiation image of the radiation detected by the radiation detection unit when the irradiation of the radiation to the object is stopped,
wherein the display control unit displays the radiation image stored by the storage unit while moving the radiation image according to the relative movement detected by the movement detection unit.

15. The radiation imaging apparatus according to claim 10, wherein, if the relative movement is detected by the movement detection unit and a speed of the relative movement is equal to or higher than a predetermined speed, the control unit stops the irradiation of the radiation to the object performed by the radiation generation unit.

16. The radiation imaging apparatus according to claim 15, further comprising a setting unit configured to set the predetermined speed based on the irradiation range detected by the irradiation detection unit.

17. A radiation imaging apparatus comprising:
a radiation generation unit configured to radiate radiation to an object;
a radiation detection unit configured to detect the radiation having passed through the object;
an irradiation detection unit configured to detect an irradiation range of the radiation radiated by the radiation generation unit; and
a movement detection unit configured to detect a relative movement of the radiation generation unit and the radiation detection unit with respect to the object,
wherein the radiation generation unit becomes resumable for radiating radiation to the object, after a stop of the irradiation of the radiation and when the relative movement detected by the movement detection unit and the irradiation range detected by the irradiation detection unit satisfy a predetermined condition.

* * * * *